US00PP19647P2

(12) United States Plant Patent
Hansen

(10) Patent No.: US PP19,647 P2
(45) Date of Patent: Jan. 20, 2009

(54) ***HOSTA* PLANT NAMED 'ROY KLEHM'**

(50) Latin Name: *Hosta hybrida*
Varietal Denomination: Roy Klehm

(75) Inventor: Hans Andrew Hansen, Waseca, MN (US)

(73) Assignee: Shady Oaks Nursery, LLC, Waseca, MN (US)

( * ) Notice: Subject to any disclaimer, the term of this patent is extended or adjusted under 35 U.S.C. 154(b) by 0 days.

(21) Appl. No.: 12/006,048

(22) Filed: Dec. 28, 2007

(51) Int. Cl.
*A01H 5/00* (2006.01)

(52) U.S. Cl. ..... Plt./353

(58) Field of Classification Search ..... Plt./353
See application file for complete search history.

*Primary Examiner*—Annette H Para
*Assistant Examiner*—Louanne C Krawczewicz Myers
(74) *Attorney, Agent, or Firm*—Penny J. Aguirre

(57) ABSTRACT

A new cultivar of *Hosta* named 'Roy Klehm', a chemically induced chimeral mutation of *Hosta* 'Summer Serenade', that is characterized by its unique variegated foliage with bright yellow-green centers and wide deep green margins comprising about one half of the leaf area. 'Roy Klehm' has an upright plant habit with leaves held horizontal on upright petioles and near white flowers held on erect flower scapes that arise above the foliage in mid summer.

2 Drawing Sheets

Botanical classification: *Hosta hybrida.*
Cultivar designation: 'Roy Klehm'.

BACKGROUND OF THE INVENTION

The present invention, *Hosta* 'Roy Klehm', relates to a new and distinct cultivar of *Hosta,* botanically known as a *Hosta hybrida,* hereinafter referred to as 'Roy Klehm'.

The inventor discovered the new cultivar, 'Roy Klehm', in summer of 2002 in a trial garden outdoors in Waseca, Minn. 'Roy Klehm' originated as a chemically induced chimeral mutation of *Hosta* 'Summer Serenade'(unpatented), 'Summer Serenade' is a chimeral mutation of 'Piedmont Gold' (not patented).

Asexual reproduction of the new cultivar was first accomplished by the inventor utilizing in vitro propagation in Waseca, Minn. in fall of 2005. Asexual reproduction of the new cultivar by division and tissue culture has shown that the unique features of 'Roy Klehm' are stable and reproduced true to type in successive generations.

SUMMARY OF THE INVENTION

The following traits have been repeatedly observed in trials in Minnesota for a period of five years and represent the characteristics of the new cultivar. These attributes in combination distinguish 'Roy Klehm' as a new and unique cultivar of *Hosta.*

1. The foliage of 'Roy Klehm' is variegated with bright yellow-green centers and wide deep green margins with margin width ranging from 2 to 8 cm. The margin comprises about one half of the leaf area.
2. 'Roy Klehm' has an upright vase-shaped plant habit with leaves held nearly horizontal on the petioles.
3. 'Roy Klehm' reaches a height of about 53 cm, exclusive of flower scapes, and a spread of about 83 cm in five years.
4. 'Roy Klehm' blooms in mid summer with near white flowers held above the foliage on erect flower scapes.

In comparison to the parent plant, 'Summer Serenade', 'Roy Klehm' has leaf margins that are significantly wider than those of 'Summer Serenade' and the plant habit of 'Roy Klehm' is upright, whereas the plant habit of 'Serenade' is mounded. The closest comparison plants to 'Roy Klehm' are chimeral mutations of gold foliaged 'Piedmont Gold': 'Satisfaction' (not patented), which differs in having the reverse variegation pattern with green centers and gold margins and in having a mounded plant habit and 'Lakeside Symphony' (not patented), which differs in having yellowish-white (lutescent) centers and pale green margins and a mounded plant habit. One could also compare 'Roy Klehm' to 'Journey's End' (U.S. Plant Pat. No. 16,895), a cultivar with a similar variegation pattern. 'Journey's End' differs from 'Roy Klehm' most significantly in having narrower margins, undulated margins, and a mounded plant habit.

BRIEF DESCRIPTION OF THE DRAWING

The accompanying colored photographs illustrate the distinct foliage characteristics of the new *Hosta.* The photographs were taken of a five year-old plant of 'Roy Klehm' as grown outdoors in a trial garden in Waseca, Minn.

The photograph in FIG. 1 was taken in late July shows a plant of 'Roy Klehm' in bloom and illustrates the plant habit.

Figure 1:
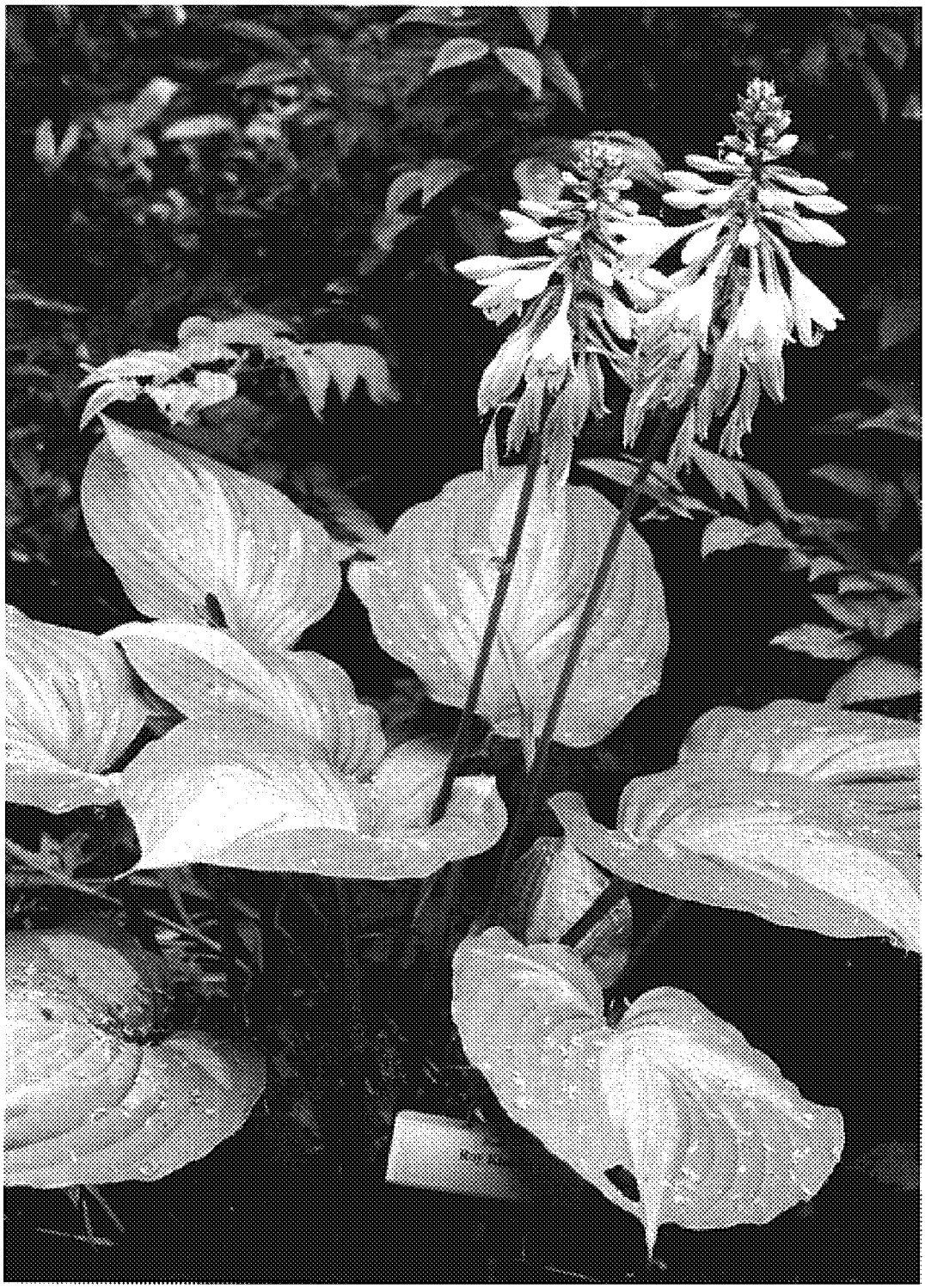
Figure 2:
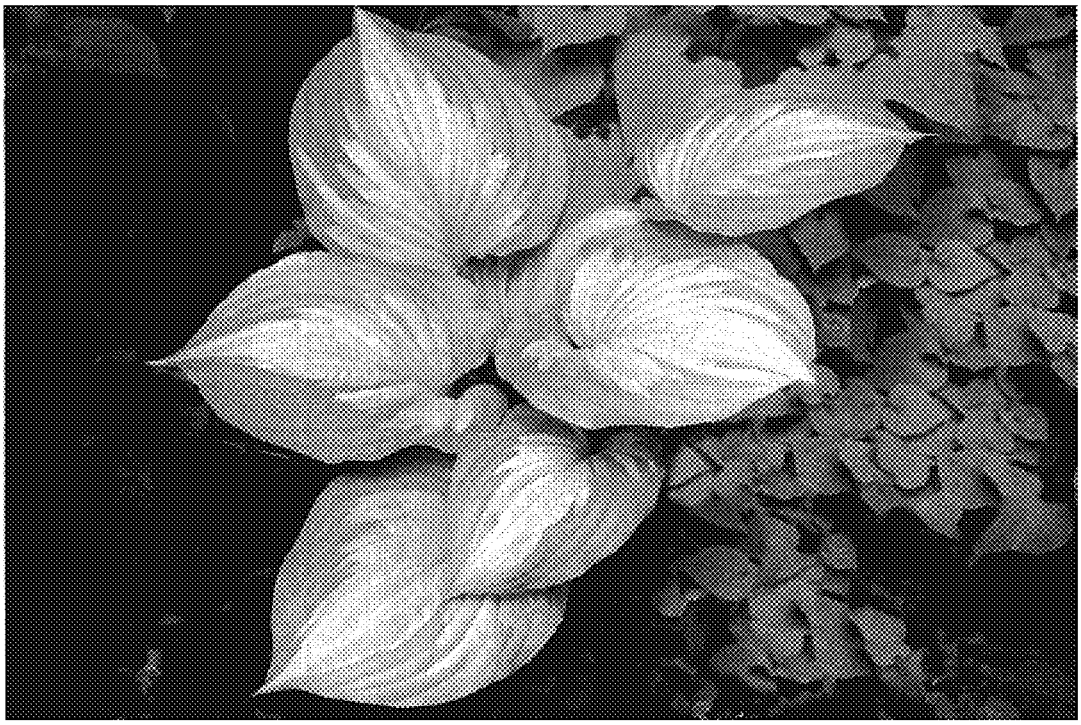

The photograph in FIG. 2 was taken in June and provides a close-up view of the foliage. Colors in the photographs may differ slightly from the color values cited in the detailed botanical description which accurately describe the colors of the new *Hosta.*

DETAILED BOTANICAL DESCRIPTION OF THE PLANT

The following is a detailed description of five year-old plants of the new cultivar as grown outdoors in Waseca, Minn. The phenotype of the new cultivar may vary with variations in environmental, climatic, and cultural conditions, as it has not been tested under all possible environmental conditions. The color determination is in accordance with the 2001 R.H.S. Colour Chart of the Royal Horticultural Society, London, England, except where general color terms of ordinary dictionary significance are used.

General description:

*Blooming period.*—About 4 weeks from late June to mid to late July.

*Plant habit.*—Herbaceous perennial, clump-forming, upright habit with leaves held horizontally.

*Height and spread.*—Reaches about 53 cm in height (excluding flower scapes) and about 83 cm in width.

*Hardiness.*—U.S.D.A. Zones 3 to 8.

*Culture.*—Light to full shade, moist soils of moderate fertility.

*Diseases and pests.*—Average substance confers some resistance to slugs. No susceptibility or resistance to diseases or other pests has been observed.

*Root description.*—Freely branched, fleshy.

*Propagation.*—In vitro propagation is the preferred method utilizing typical methods for *Hosta,* division are also possible.

*Root development.*—Rooted transplants from tissue culture fully develop in a 96-cell liner in about 6 to 8 weeks in a greenhouse with average temperatures of about 70° F.

*Growth rate.*—Moderate.

Foliage description:

*Leaf shape.*—Broadly ovate.

*Leaf division.*—Simple.

*Leaf base.*—Cordate.

*Leaf apex.*—Cuspidate.

*Leaf venation.*—10 to 11 pairs of veins, camptodrome pattern, impressed on upper surface and raised on lower surface, color matches leaf coloration on upper surface, 191C on lower surface.

*Leaf margins.*—Entire.

*Leaf aspect.*—Flat.

*Leaf attachment.*—Petiolate.

*Leaf arrangement.*—Basal, radiate spirally from base.

*Leaf surface.*—Glabrous on upper surface, slightly glaucous on lower surface.

*Leaf substance.*—Average.

*Leaf orientation.*—Held nearly horizontal on upright petioles.

*Leaf color.*—Spring foliage upper surface; centers blending of 144A and 144B, margins 137B (slightly more green), spring foliage lower surface; centers color between 144A and 138B, margins 191A, summer foliage upper surface; centers 151B (slightly lighter) with shadings and intermediate area of 144A, margins 137B, summer foliage lower surface; centers 144A, margins 137B.

*Leaf variegation pattern.*—Margins range from 2 to 8 cm in width, comprising about one half of the leaf area, center area has a primary area that is elliptic in shape with basal markings radiating out from the base on either side of the middle pattern.

*Leaf size.*—About 29 cm in length, about 20 cm in width.

*Leaf quantity.*—About 6 per shoot (eye).

*Petiole size.*—About 39 cm in length, about 9 mm in width.

*Petiole color.*—Inner surface 144A, outer surface 144D, glabrous surface.

*Petiole surface.*—Glabrous.

*Petiole shape.*—Sulcate.

Flower scape description:

*Scape shape.*—Round, solid.

*Scape number.*—One per mature eye under normal growing conditions.

*Scape posture.*—Held upright.

*Scape size.*—Average of 86 cm in length, average of 6 mm in width.

*Scape color.*—144B.

*Scape surface.*—Glabrous and satiny with ridges on portion with blooms.

*Leafy bracts.*—Average of two, basal leaf is broadly ovate in shape narrowing to a basal portion that is linear and curved inward, average of 9 cm in length and 3 cm in width, apiculate apex, truncate base, entire margin, more distal leave is lanceolate in shape with acute apex, truncate base and entire margin, coloration and surface of bracts is similar to vegetative leaves.

Flower description:

*Inflorescence type.*—Terminal racemes of single bell-shaped flowers on elongated scapes.

*Lastingness of inflorescence.*—About 4 weeks from first opening bloom to fading of last opening bloom, individual blooms last about one day.

*Inflorescence height.*—About 28 cm.

*Inflorescence width.*—About 7 cm.

*Flower shape.*—Bell-shaped.

*Flower number.*—Average of 52 per scape.

*Flower internode length.*—Average of 3.5 mm, longer on basal region to tightly congested at terminal.

*Flower fragrance.*—None.

*Flower buds.*—Spathulate in shape, average of 4.2 cm in length and 1.2 cm in diameter, surface is glabrous and somewhat waxy, color at maturity 155C lightly suffused with 85C to 85D.

*Flower size.*—About 5 cm in length and about 1.8 cm in diameter.

*Flower color.*—155C with light suffusion of 85D (nearly white).

*Pedicels.*—About 1 cm in length and 2 mm in diameter, closest to 194B in color, glabrous texture.

*Perianth features.*—Comprised of 6 tepals, 3 interior and 3 exterior, overlapping and fused from the middle of the expanded region to base of tube.

*Tepals.*—Lanceolate in shape, about 4 cm in length, about 7 mm in width, color of outer and inner surfaces 155C lightly suffused with 85D, glabrous surfaces, entire margins, fused base, acute apex.

*Floral bracts.*—One per flower, broadly lanceolate in shape, average of 1.8 cm in length and 8 mm in width, color of upper and lower surface 144A with base 144D, entire margin, truncate base (sessile to scape), glabrous surface.

Reproductive organs:

*Gynoecium.*—3 Pistils, style is variable in length ranging from 2 to 4.5 cm, about 0.5 mm in width, rarely extended beyond perianth, and 158C in color, stigma is pilose, 0.7 mm in diameter and length and 158C in color, ovary is superior, compound, composed of 3 locules, about 7 mm in length and 3 mm in width, 144C in color.

*Androecium.*—6 stamens, filament is 158B in color, about 5.2 cm in length and 0.7 mm in width, extends about 1 cm beyond perianth, anthers are 4.2 mm in length and 1.5 mm in width, attachment is versatile, 202A in color, dehiscence is longitudinal, pollen is abundant and 17A in color.

*Fruit*.—Capsule, 3-chambered, about 3 cm in length, 8 mm in width, between 137A and 144A in color.

*Seeds*.—About 12 seeds per capsule, about 8 mm in length and 2 mm in width, 202A in color.

It is claimed:

1. A new and distinct cultivar of *Hosta* plant named 'Roy Klehm' as herein illustrated and described.

* * * * *